(12) United States Patent
Louban et al.

(10) Patent No.: US 8,471,207 B2
(45) Date of Patent: Jun. 25, 2013

(54) METHOD FOR THE AUTOMATIC INSPECTION OF A WELDING SEAM BY MEANS OF HEAT FLOW THERMOGRAPHY

(76) Inventors: Roman Louban, Crailsheim (DE); Christoph Döttinger, Erlangen (DE); Peter Stolz, Fürth (DE); Manfred Böhm, Wendelstein (DE)

(*) Notice: Subject to any disclaimer, the term of this patent is extended or adjusted under 35 U.S.C. 154(b) by 724 days.

(21) Appl. No.: 12/667,683

(22) PCT Filed: Jul. 3, 2008

(86) PCT No.: PCT/EP2008/005429
§ 371 (c)(1),
(2), (4) Date: Jan. 4, 2010

(87) PCT Pub. No.: WO2009/003702
PCT Pub. Date: Jan. 8, 2009

(65) Prior Publication Data
US 2010/0163732 A1   Jul. 1, 2010

(30) Foreign Application Priority Data

Jul. 4, 2007  (DE) .......................... 10 2007 031 184
Jul. 4, 2007  (DE) .......................... 10 2007 031 206
Jul. 4, 2007  (DE) .......................... 10 2007 031 215

(51) Int. Cl.
*G01J 5/02*  (2006.01)
*G01K 17/00*  (2006.01)

(52) U.S. Cl.
USPC ..................... 250/341.6; 250/341.8; 374/30

(58) Field of Classification Search
USPC ............... 250/341.6, 341.7, 341.8; 374/4, 374/30; 73/170.12, 850
See application file for complete search history.

(56) References Cited

U.S. PATENT DOCUMENTS 5,631,465 A    5/1997 Shepard
5,654,977 A *  8/1997 Morris .............................. 374/4
(Continued)

FOREIGN PATENT DOCUMENTS

DE    1788563 U    5/1959
DE    3339182 C1   4/1985
(Continued)

OTHER PUBLICATIONS

Soille,"Morphologisch Bildverarbeitung," 1998, pp. 238-239.
(Continued)

*Primary Examiner* — David Porta
*Assistant Examiner* — Kenneth J Malkowski
(74) *Attorney, Agent, or Firm* — Nixon Peabody LLP; Joseph Bach, Esq.

(57) ABSTRACT

In a method for the automatic inspection of a welding seam using heat flow thermography, a feature vector is established which represents a time course of a detected heat flow. The feature vector is used to determine, from a series of thermal images, a first characteristic thermal image, which corresponds to a minimum heat flow through an object to be examined, and a second characteristic thermal image, which corresponds to a maximum heat flow through the object, wherein a heat flow directly from an excitation source has already dissipated. A suitable thermal image is used from the series of thermal images to detect and evaluate the welding seam in relation to defects of various defect types, for each defect type, the characteristic thermal images being used as references to determine the respective suitable thermal image.

19 Claims, 3 Drawing Sheets

U.S. PATENT DOCUMENTS

| | | | |
|---|---|---|---|
| 5,963,662 A * | 10/1999 | Vachtsevanos et al. | 382/150 |
| 7,474,798 B2 | 1/2009 | Seger et al. | |
| 2003/0193987 A1 * | 10/2003 | Zalameda et al. | 374/5 |
| 2004/0028113 A1 | 2/2004 | Schlagheck et al. | |
| 2006/0239528 A1 | 10/2006 | Camus et al. | |

FOREIGN PATENT DOCUMENTS

| | | |
|---|---|---|
| DE | 242099 A1 | 1/1987 |
| DE | 19703484 A1 | 8/1998 |
| DE | 10004049 A1 | 8/2000 |
| DE | 10150633 A1 | 4/2003 |
| DE | 10202163 A1 | 7/2003 |
| DE | 10222786 A1 | 11/2003 |
| DE | 10326377 B3 | 12/2004 |
| DE | 202004003775 U1 | 7/2005 |
| DE | 102005018327 A1 | 10/2006 |
| DE | 102005026625 A1 | 12/2006 |
| DE | 102007031184 A1 | 1/2009 |
| DE | 102007031215 A1 | 1/2009 |
| DE | 102007031206 B3 | 2/2009 |
| GB | 2346688 A | 8/2000 |
| JP | 63013668 A | 1/1988 |

OTHER PUBLICATIONS

Maldague,"Theory and practice of Infrared technology for nondestructive testing," Wiley series in microwave and optical engineering, 2001, John Wiley & Sons.

* cited by examiner

METHOD FOR THE AUTOMATIC INSPECTION OF A WELDING SEAM BY MEANS OF HEAT FLOW THERMOGRAPHY

FIELD OF THE INVENTION

The invention relates to a method for the automatic inspection of a welding seam by means of heat flow thermography, in which an object, which is to be examined, with a welding seam is provided, wherein the object is excited by means of at least one excitation source, and the heat flow produced by the excitation is detected in a series of thermal images using at least one infrared sensor.

BACKGROUND OF THE INVENTION

In the automobile industry, radiation-assisted connecting methods are extensively used for body construction, such as, for example, electron beam, laser beam and laser hybrid welding methods. The number of welding connections, in particular including the welding seams, has significantly increased in past decades. Accordingly, there is a great need in the automobile industry for systems allowing automatic inspection and control of welding seams.

The most varied types of defects may occur in the production of welding seams. Defects of this type are, for example, a length which is too short, insufficient full penetration welding, a crack, a cut, a hole, a pore or a blow hole. A reliable inspection of welding seams assumes that defects of the most varied types can be reliably detected and recognised.

A method for checking a welding seam is known from DE 100 04 049 A1, in which the heat radiation in the region of the welding seam is detected as an image with the aid of a digital infrared camera and compared with a previously recorded reference image using a computer. The quality of the welding seam is assessed using the comparison. However, this method does not ensure a reliable inspection of the welding seam, in particular if defects of various types occur.

Furthermore, a method for automatic destruction-free checking of a welding seam is known from DE 103 26 377 B3, in which the welding seam is heated and a thermography sensor is moved on a checking path, which detects the temperature values at each point of the checking path. The temperature values may be evaluated as quality features of the welding seam and shown in a position-related manner with respect to the welding seam. This method does not ensure reliable inspection of the welding seam either, in particular if defects of various types occur.

SUMMARY OF THE INVENTION

The invention is therefore based on the object of providing a method for the automatic inspection of a welding seam using heat flow thermography, which ensures reliable detection and evaluation of the welding seam in relation to defects of various types.

This object is achieved by a method for the automatic inspection of a welding seam using heat flow thermography, wherein a feature vector is produced, which is a time course of the detected heat flow, wherein a first characteristic thermal image is dynamically determined from the series of thermal images using the feature vector, and the first characteristic thermal image has a minimum heat low through the object, and a second characteristic thermal image is dynamically determined from the series of thermal images using the feature vector, and the second characteristic thermal image has a maximum heat flow through the object, and wherein a heat flow directly from the excitation source to the characteristic thermal images has already dissipated, if it is apparent from the series of thermal images, and a suitable thermal image from the series of thermal images is used to detect and evaluate the welding seam with respect to defects of various defect types, for each defect type, the characteristic thermal images being used as references to determine the respective suitable thermal image. It was recognized according to the invention that defects of various types, depending on the type of defect, can best be recognized at different times. Accordingly, during the investigation of the welding seam, at least one suitable thermal image from the series of thermal images on which defects of this type can best be seen, is used for each defect type. The welding seam is therefore detected and evaluated—depending on the defect type—at a suitable time, in each case. To establish the respectively suitable thermal image, the characteristic thermal images from the recorded series of thermal images are used as references. The characteristic thermal images are dynamically determined with the aid of the feature vector. Dynamically means that, for each newly recorded series of thermal images of the same welding seam or another welding seam, the characteristic thermal images are redetermined. The feature vector is a time course of the detected heat flow. This means that the feature vector contains a value for the heat flow for each individual thermal image of the detected series of thermal images. The heat flow is determined for each individual thermal image, for example, within a test region by averaging over all the pixels of the infrared sensor in this test region. The heat flow has minima and maxima in the feature vector as a function of the recording time of the thermal images, in other words the image number of the thermal images. This is due to the fact that the heat flow shown in the feature vector is composed of a heat flow through the welded material, in other words through the object with the welding seam, and from a heat flow directly from the excitation source—if this is apparent in the series of thermal images.

To determine the first characteristic thermal image, in the feature vector, the first minimum is determined, from which the heat flow through the welded material begins to grow and the disruptive heat flow from the excitation source has already dissipated, if existing. The first characteristic thermal image having a minimal heat flow through the object is produced by means of the associated time, in other words the associated image number. To determine the second characteristic thermal image, the absolute maximum of the feature vector is determined in relation to thermal images, which were recorded later with respect to time than the first characteristic thermal image. From this maximum, the heat flow through the welded material begins to drop, the disruptive heat flow from the excitation source having already dissipated. The second characteristic thermal image is produced from the time associated with the maximum, in other words the associated image number. This has a maximum heat flow through the object. Thus, it is ensured on the two characteristic thermal images that the heat flow directly from the excitation source has already dissipated if this is apparent in the series of thermal images. The characteristic thermal images therefore ensure a reliable reference for automatically determining a respectively suitable thermal image that is most suitable for defects of a certain defect type. The inspection of the welding seam can thus take place reliably for defects of the most varied types as it is ensured that the most suitable thermal image, on which defects of this type can best be seen, is used for each defect type.

The method according to the invention may for example be applied to an object made of at least two joint partners, being interconnected by one or more welding seams. The joint partners may be designed as metal sheets.

A method wherein the second characteristic thermal image is used for detecting defects of a first defect type as the suitable thermal image, the defects of the first type being geometric defects of the welding seam, ensures reliable detection and evaluation of the welding seam in relation to geometric defects, such as, in particular, maintaining a required length and/or width. As the second characteristic thermal image has a maximum heat flow through the object, the welding seam on this thermal image may be best detected and evaluated with regard to its geometric dimensions, such as, for example length and/or width.

A method wherein the second characteristic thermal image is used for detecting defects of a first defect type as the suitable thermal image, the defects of the first defect type being geometric defects of the welding seam, ensures reliable detection and evaluation of the welding seam in relation to geometric defects, such as, in particular, maintaining a required length and/or width. As the second characteristic thermal image has a maximum heat flow through the object, the welding seam on this thermal image may be best detected and evaluated with regard to its geometric dimensions, such as, for example length and/or width.

A method according to claim 3 wherein a start image being used for detecting defects of a first defect type is dynamically detected in such a way, that the start image is located between the first and the second characteristic thermal image and has a heat flow, which exceeds a first threshold value in the time course of the detected heat flow for the first time, wherein for the first threshold value:

$$W_{start\_thd} = W_{min} + (W_{max} - W_{min}) \cdot \theta.$$

applies, wherein
  $W_{start\_thd}$ means first threshold value,
  $W_{min}$ means minimum heat flow, having the first characteristic thermal image,
  $W_{max}$ means maximum heat flow, having the second characteristic thermal image,
  $\theta$ means separation factor,
wherein a part series of suitable thermal images from the series is selected from the start image and a series length, wherein a result image is obtained from the part series, and wherein the defects of the first defect type are geometric defects of the welding seam and the result image is used to detect and evaluate them, ensures reliable detection and evaluation of the welding seam in relation to geometric defects, such as, in particular, the maintaining of a required length and/or width. In objects which are still hot after welding, the detection and evaluation of the welding seam in relation to geometric defects may take place with greater reliability with the aid of a suitable result image. Determining the start image ensures that the result image is produced without disturbance. This means that the determination of the start image between the first and second characteristic thermal image ensures that the part series of suitable thermal images, also called a part image series, does not contain any direct heat flow from the excitation source. The separation factor is determined for this purpose in such a way that the latter ensures reliable delimitation of a part series which is without disturbance. The start image is dynamically determined by means of the feature vector, which means that the start image is redetermined for each newly recorded series of thermal images. The result image may be of the most varied types, such as, for example, an amplitude or a phase image. The obtaining of amplitude and phase images is known in principle and described in "*Theory and Practice of Infrared Technology for Non-destructive Testing*" (Xavier P.V. Maldague, John Wiley & Sons, Inc. 2001), to which reference is made. An amplitude image is preferably used as the result image for the detection and evaluation of the welding seam in relation to geometric errors.

A separation factor being determined in the range between 0 and 1, in particular between 0.1 and 0.15, ensures a reliable separation between a noise signal and a significant signal of the heat flow. Accordingly, a reliable selection of a part series of thermal images is ensured, which does not contain any direct heat flow from the excitation source. In practice, a separation factor of $1/e^2 \approx 0.135$ has proven successful, in particular, wherein e is the Euler's number.

Dynamically determining a series length, wherein at least two images from an image quantity, which contains the first characteristic thermal image, the second characteristic thermal image and the start image, are used as references, ensures reliable detection and evaluation of the welding seam using the result image. As the characteristic thermal images and the start image are dynamically determined from the series of thermal images, the series length of the part series can also be determined dynamically and automatically. Dynamically means that the series length is redetermined for each newly recorded series of thermal images. The series length may, for example, be selected as twice the length between the start image and the second characteristic thermal image. Furthermore, the series length may be selected, for example, as the next greatest length, which is a power of two and exceeds the length between the characteristic thermal images. In each case, the series length is to be determined such that the part series does not exceed the detected series of thermal images. The determining of series lengths to produce a result image is described, for example, in "*Theory and Practice of Infrared Technology for Non-destructive Testing*" (Xavier P.V. Maldague, John Wiley & Sons, Inc. 2001), to which reference is made.

A method, wherein a thermal image, which was detected before the first characteristic thermal image and has a maximum heat flow of the excitation source is used for detecting defects of a second defect type as a suitable thermal image, the defects of the second defect type being continuous defects of the welding seam, ensures reliable detection and evaluation of the welding seam in relation to continuous defects, such as, for example holes. To detect and evaluate defects continuing through the welded material, the last thermal image before the first characteristic thermal image is used, for example, which has a maximum heat flow directly from the excitation source, if this heat flow is apparent in the series of thermal images.

Continuous defects may best be recognised recognized on the basis of the maximum heat flow directly from the excitation source on this thermal image.

A method, wherein a thermal image, which is located between the first and the second characteristic thermal image and has a heat flow, which exceeds a second threshold value in the time course of the detected heat flow for the first time, is used for detecting defects of a third defect type as the suitable thermal image, wherein for the second threshold value:

$$W_{inside\_thd} = W_{min} + (W_{max} - W_{min}) \cdot \zeta.$$

applies, wherein
  $W_{inside\_thd}$ means second threshold value,
  $W_{min}$ means minimum heat flow, having the first characteristic thermal image,
  $W_{max}$ means maximum heat flow, having the second characteristic thermal image,
  $\zeta$ means first heat flow factor, the defects of the third defect type being defects located in the interior of the welding seam, ensures reliable detection and evaluation of defects, which are located in the interior of the welding seam, such as, for example pores. Using the first heat flow factor, a thermal image may be certainly and reliably detected, which is located between the characteristic thermal images and is best suited for the detection and evaluation of defects located in the interior of the welding seam.

A first heat flow factor being determined in the range between 0 and 1, in particular between 0.6 and 0.9, has proven successful in practice, as the defects located in the interior of the welding seam impair the heat flow in this region.

A method, wherein a thermal image, which is located between the first and the second characteristic thermal image and has a heat flow, which exceeds a third threshold value in the time course of the detected heat flow for the first time, is used for detecting defects of a fourth defect type as the suitable thermal image, wherein for the third threshold value:

$$W_{surf\_thd} = W_{min} + (W_{max} - W_{min}) \cdot \delta.$$

applies, wherein
$W_{surf\_thd}$ means third threshold value,
$W_{min}$ means minimum heat flow, having the first characteristic thermal image,
$W_{max}$ means maximum heat flow, having the second characteristic thermal image, and
$\delta$ means second heat flow factor,
the defects of the fourth defect type being surface defects of the welding seam, ensures reliable detection and evaluation of the welding seam in relation to surface defects, such as, for example, cracks, cuts or blow holes. A thermal image which is located between the characteristic thermal images and is best suited for detecting and evaluating surface defects can be certainly and reliably selected from the series of thermal images using the second heat flow factor.

A second heat flow factor being determined in the range between 0 and 1, in particular between 0.1 and 0.4, has proven successful in practice, as surface defects favor the heat flow because of the small material thickness in this region.

A method, wherein at least one of the images, which are used to detect and evaluate the welding seam in relation to defects of various defect types, is converted into an 8 bit image, wherein a histogram of the image is produced, a first portion relevant to information of a first intensity region, which corresponds to an image object, is determined from the histogram, wherein a first lower limit value and a first upper limit value are dynamically determined, and wherein the first limit values delimit first characteristic area portions of an area of the histogram corresponding to the first intensity region, a second portion relevant to information of a second intensity region, which corresponds to an image background, is determined from the histogram, wherein a second lower limit value and a second upper limit value are dynamically determined, and wherein the second limit values delimit second characteristic area portions of an area of the histogram corresponding to the second intensity region, and the portions relevant to information are used as a basis for the conversion of the image to be examined into an 8 bit image, allows automatic conversion, which is adequate with regard to the image content, of a thermal image or result image into an 8 bit image conventional for image processing. An image of this type can be used for visual control or further automatic processing. Owing to the adequate conversion in accordance with the image content, the image objects including their characteristic features, such as, for example their edge, structure, shape and size, can be shown in an undistorted manner on their background in the converted image. Image objects are for example the welding seam and/or the defects of the different defect types. The absolute limit values, which delimit the portion relevant to information of the object intensity region in the histogram, and the absolute limit values, which delimit the portion relevant information of the background intensity region in the histogram, are dynamically determined from the calculated histogram of the respective image. Dynamically means that the absolute limit values are redetermined for each image to be converted. In this case, the absolute lower limit values intersect a respective characteristic area portion of the histogram area of the object intensity region or of the background intensity region from below and the absolute upper limit values intersect a respective characteristic area portion from above. Thus, a basis, relevant to information, of the content of the highly dynamic thermal image or result image is detected, which is used for the dynamic conversion of this image. The individual outlier pixels lying outside this basis, which have extreme intensity values or random noise values, then have no negative influence on the dynamic conversion of this image.

A development, wherein the first characteristic area portions in relation to the area corresponding to the first intensity region are determined in the range between 0 and 0.5, in particular between 0.05 and 0.4, ensures reliable detection of the portion relevant to information of the object intensity region. The histogram may be regarded as a combination of normal distribution densities according to Gauss of the image object to be examined, the image background and the occurring disturbances. Accordingly, the first characteristic area portions may be compared with a value of the probability integral of the normal distribution according to Gauss. The first characteristic area portions may, in each case, for example be a 2.5% area fraction of the area corresponding to the object intensity region, so the remaining area portion, relevant to information, of the object intensity region is 95%. In general, the first characteristic area portions are determined empirically and are, for example, in the range between 0 and 0.5, in particular between 0.05 and 0.4.

A development, wherein the second characteristic area portions in relation to the area corresponding to the second intensity region are determined in the range between 0 and 0.5, in particular between 0.05 and 0.4, ensures reliable detection of the portion relevant to information of the background intensity region. The histogram may be regarded as a combination of normal distribution densities in accordance with Gauss of the image object to be examined, the image background and the occurring disturbances. Accordingly, the second characteristic area portions may be compared with a value of the probability integral of the normal distribution in accordance with Gauss. The second characteristic area portions may, for example, in each case be a 2.5% area portion of the area corresponding to the background intensity region, so the remaining area portion relevant to information of the background intensity region is 95%. Generally, the second characteristic area portions are empirically determined and are in the range between 0 and 0.5, in particular between 0.05 and 0.4.

A method, wherein the characteristic area portions are determined independently of one another, allows flexible and reliable determination of the basis relevant to information of the recorded thermal image or the result image.

A development, wherein at least one of the feature vector and the histogram are processed with the aid of at least one morphological filter, ensures reliable processing and evaluation of the feature vector and/or of the histogram. Both the feature vector, which represents a time course of the heat flow recorded, and the histogram of the highly dynamic thermal image or result image form curves to be examined. The processing of these curves by means of at least one morphological filter can ensure perfect detection and correct evaluation of the characteristic points or point ranges on these disturbance-rich curves. The characteristic points are, for example, the local and/or the absolute minima or maxima. The watershed transformation can be used, for example, as the morphological filter, which is described in the book *"Morphologische Bildverarbeitung"* by Pierre Soille, Springer Verlag, Berlin 1998, to which reference is made.

Further features, advantages and details of the invention emerge from the following description of an embodiment with the aid of the drawings.

Figure 1:
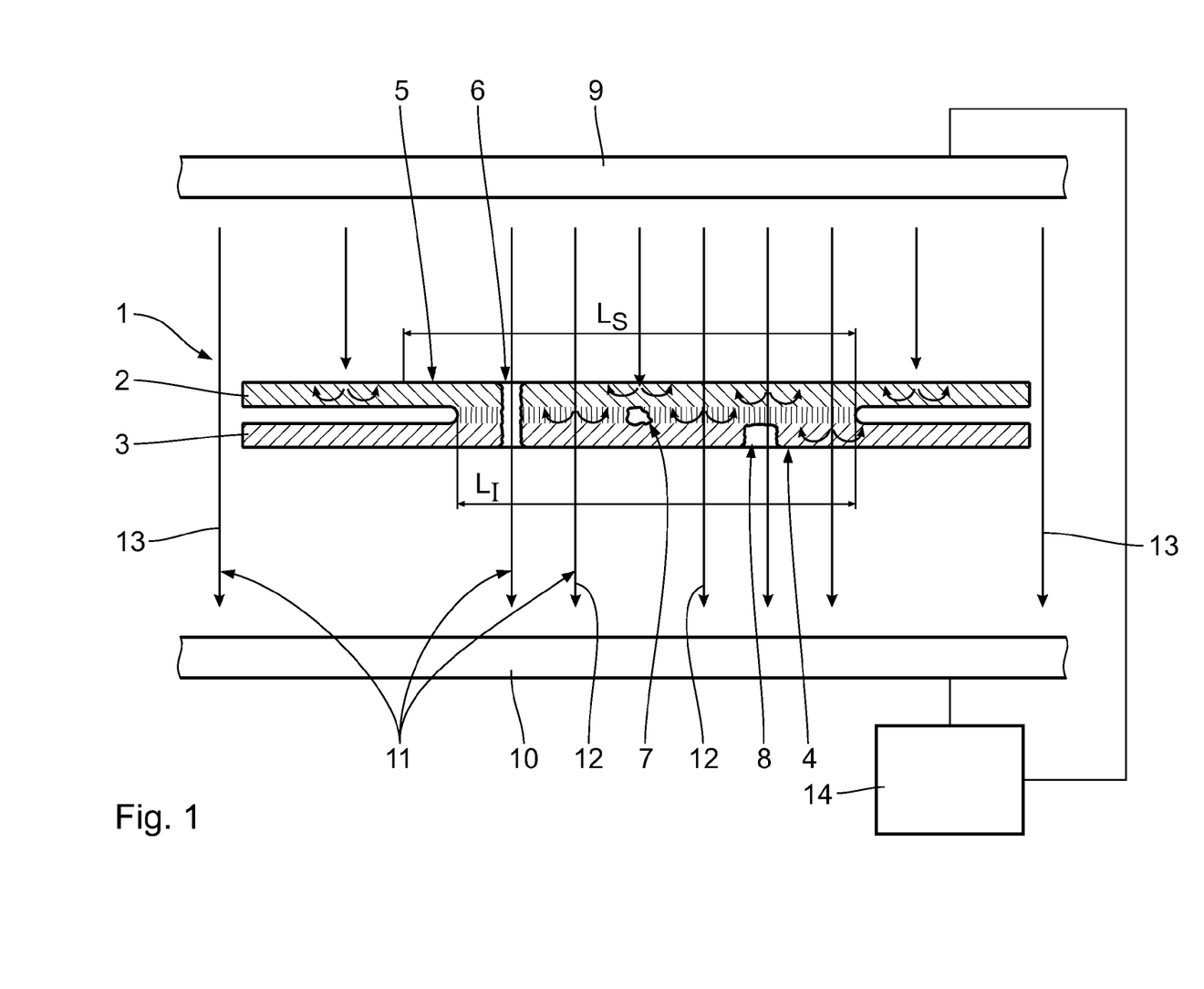
FIG. 1 shows a sectional view through a welding seam with defects of various types connecting two joint partners.

DESCRIPTION OF THE PREFERRED EMBODIMENT:

An object 1 to be checked has a first joint partner 2 and a second joint partner 3, which are connected to one another by a welding connection in the form of a welding seam 4. The joint partners 2, 3 are configured as metal sheets. The welding seam 4 was produced, for example, by means of an electron beam, laser beam or laser hybrid welding method. The material of the joint partners 2, 3 is fused together in the region of the welding seam because of the welding process. The object 1 with the welding seam 4 will also be designated the welded material below.

The welding seam 4 has a plurality of defects of various types. As an example of a first defect type, the welding seam 4 has a geometric defect 5. The geometric defect 5 is a deviation of a desired length $L_S$ from an actual length $L_I$. Furthermore, the welding seam 4, as a defect of a second defect type, has a continuous defect 6 in the form of a hole through the welding seam 4. As a defect of a third type, the welding seam 4 has an inner defect 7, which is configured as a pore, and is located in the interior of the welding seam 4. As a defect of a fourth defect type, the welding seam 4 moreover has a surface defect 8, which is configured as a cut on the surface of the welding seam 4.

An excitation source 9 and an infrared sensor 10 are arranged on opposing sides of the object 1. Preferably, the infrared sensor 10 is arranged on the side of the object 1 from which the welding of the two joint partners 2, 3 took place, thus, for example, from the side of the laser beam. The object 1 and the welding seam 4 to be inspected are excited by means of the excitation source 9. A heat flow 11 is produced, which is detected by the infrared sensor 10 in a series of thermal images recorded one after the other. The detected heat flow 11 is composed of a heat flow 12 through the object 1 and a heat flow 13 directly from the excitation source 9.

To evaluate the detected series of thermal images, an arithmetic unit 14 is provided, which is connected to the excitation source 9 and the infrared sensor 10.

The method for the automatic inspection of the welding seam 4 using heat flow thermography is described below. The object 1 with the welding seam 4 is excited by means of the excitation source 9, which, for example, produces a flash. The heat flow 11 produced by the excitation is recorded by means of the infrared sensor 10, passed on to the arithmetic unit 14 and examined there.

Figure 2:
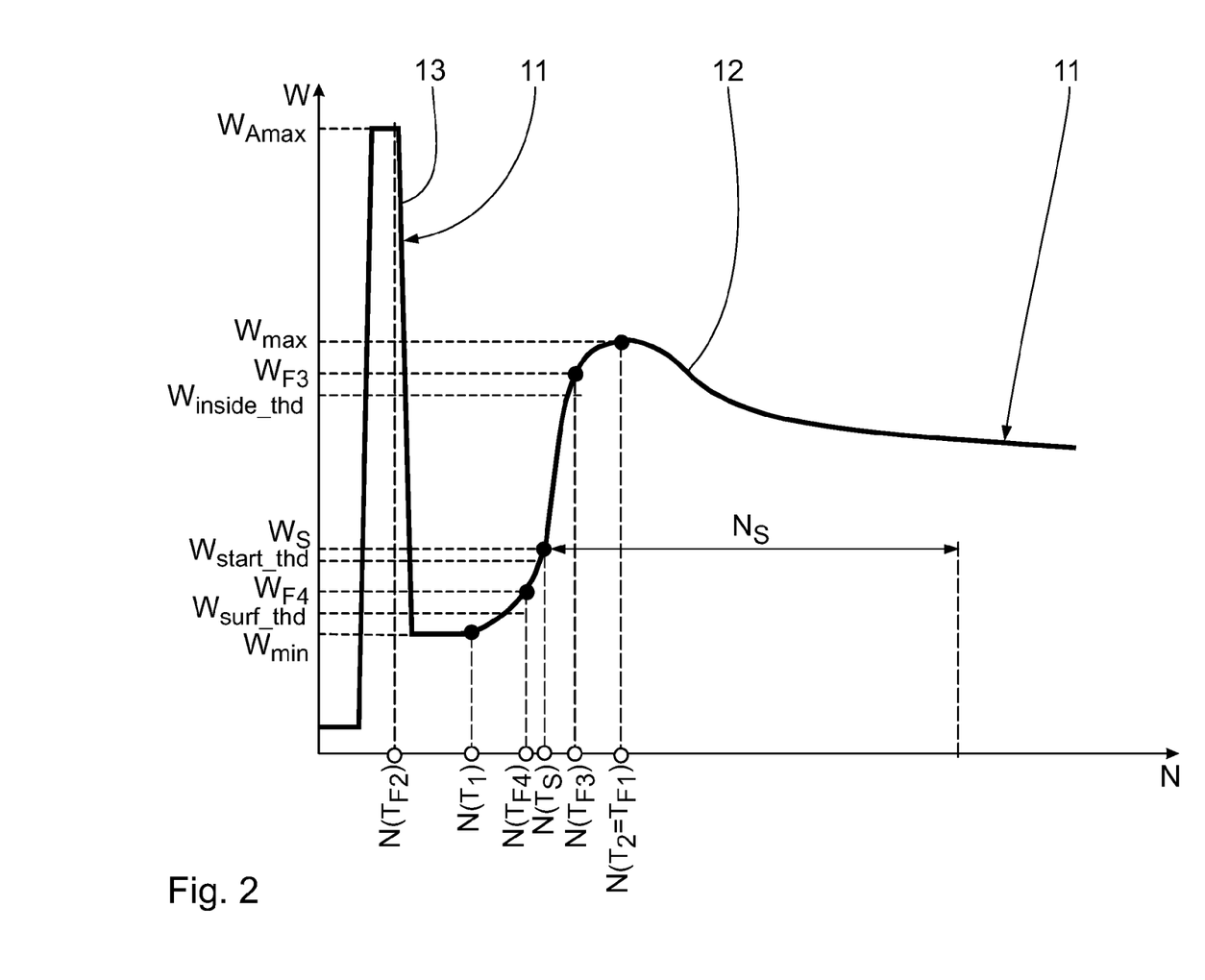
FIG. 2 shows a schematic view of a feature vector, which shows a time course of a recorded heat flow.

A feature vector W(N) is produced in the arithmetic unit 14 which is a time course of the detected heat flow 11. An image number N is associated with each thermal image from the recorded series. A heat flow value W is calculated for each thermal image. The heat flow value W is produced, for example, as a mean value of the image values, which have the pixels of the infrared sensor 10 in a test region. The feature vector W(N) is produced by plotting the calculated heat flow values W over the image number N of the corresponding thermal image. The feature vector W(N) is shown in FIG. 2.

The feature vector W(N) is a time course of the recorded heat flow 11. Accordingly, the heat flow 12 through the object 1 and the heat flow 13 directly from the excitation source 9 is shown in the feature vector W(N).

Depending on the recording time, in other words the image number N, the time course of the heat flow in the feature vector W(N) has minima and maxima. The welding seam to be examined and the defects 5, 6, 7, 8 which have occurred can be recognised, depending on the defect type, at different recording times, in other words on different thermal images. In order to ensure the best possible detection and evaluation of the welding seam 4, a suitable thermal image $T_{F1}$ to $T_{F4}$ is determined in each case for the defects 5, 6, 7, 8 for each defect type. For this purpose, a first characteristic thermal image $T_1$ and a second characteristic thermal image $T_2$ are firstly determined. The first characteristic thermal image $T_1$ is determined in such a way that a minimum is determined in the feature vector W(N), from which the heat flow 12 through the welded material starts to grow and the disturbing heat flow 13 from the excitation source 9 has already dissipated. The minimum corresponds to a minimum heat flow $W_{min}$ through the object 1, which the first characteristic thermal image $T_1$ has. The first characteristic thermal image $T_1$ is produced with the aid of the feature vector W(N) from the image number $N(T_1)$ associated with the minimum heat flow $W_{min}$.

Thereafter, the absolute maximum in the feature vector W(N) is detected in relation to thermal images of the series recorded later with respect to the characteristic thermal image $T_1$. From this maximum, the heat flow 12 through the welded material begins to drop. The maximum heat flow W. through the object 1 is thus determined, which the second characteristic thermal image $T_2$ has. The second characteristic thermal image $T_2$ is produced with the aid of the material vector W(N) from the image number $N(T_2)$ associated with the maximum heat flow $W_{max}$.

The welding seam 4 can best be detected and evaluated on the second characteristic thermal image $T_2$, as the heat flow 12 through the welded material has an absolute maximum thereon, the heat flow 13 from the excitation source 9 having already dissipated. The geometric defect 5, which is a defect of a first type can best be detected and evaluated on the second characteristic thermal image $T_2$. The second characteristic thermal image $T_2$ is thus the suitable thermal image $T_{F1}$ for defects of the first defect type.

The continuous defect 6, which is a defect of a second defect type can, on the other hand, best be detected and evaluated on the last thermal image, which was recorded before the first characteristic thermal image $T_1$ and corresponds to a maximum heat flow W Amax directly from the excitation source 9. This thermal image is the suitable thermal image $T_{F2}$, which is best suited to the detection and evaluation of defects of the second defect type. The thermal image $T_{F2}$ is produced from the image number $N(T_{F2})$ associated with the maximum heat flow $W_{Amax}$ of the excitation source 9.

To detect and evaluate the inner defect 7, representing a defect of a third defect type, a thermal image $T_{F3}$ between the characteristic thermal images $T_1$, $T_2$ is used, which corresponds to a heat flow $W_{F3}$, the value of which exceeds a threshold value $W_{inside\_thd}$ (inside threshold) in the time course of the recorded heat flow 11 for the first time. For the threshold value $W_{inside\_thd}$:

$$W_{inside\_thd} = W_{min} + (W_{max} - W_{min}) * \zeta$$

applies, wherein $\zeta$ is designated the first heat flow factor, which ensures reliable recognition of the inner defect 7. The first heat flow factor $\zeta$ is determined empirically and lies in the range between 0 and 1, in particular between 0.6 and 0.9. The thermal image $T_{F3}$, which is best suited to detect and evaluate defects of the third defect type, is produced from the image number $N(T_{F3})$ associated with the heat flow $W_{F3}$.

To detect and evaluate the surface defect 8, which is a defect of a fourth defect type, a thermal image $T_{F4}$ between the characteristic thermal images $T_1$, $T_2$ is used, which corresponds to a heat flow $W_{F4}$, the value of which exceeds a threshold value $W_{surf\_thd}$ (surface threshold) in the time course of the recorded heat flow 11 for the first time. For the threshold value $W_{surf\_thd}$:

$$W_{surf\_thd} = W_{min} + (W_{max} - W_{min}) * \zeta$$

applies, wherein $\delta$ is designated as the second heat flow factor, which ensures reliable recognition of the surface defect 8. The first heat flow factor $\delta$ is determined empirically and lies in the range between 0 and 1, in particular between 0.1 and 0.4. The thermal image $T_{F4}$, which is best suited to detect and evaluate defects of the fourth defect type, is produced from the image number $N(T_{F4})$ associated with the heat flow $W_{F4}$.

A suitable thermal image $T_{F1}$ to $T_{F4}$ is thus in each case dynamically determined and provided for the detection and evaluation of defects of various types. The characteristic thermal images $T_1$, $T_2$ are used as references for determining the respectively suitable thermal image $T_{F1}$ to $T_{F4}$.

Alternatively, for example, defects of the first defect type can also be detected and evaluated on a suitable result image, which is obtained from a part series of suitable thermal images, the part series being selected from the detected series of thermal images. The part series is produced from a start image $T_S$ and a series length $N_S$. In order to ensure a reliable exclusion of the part series or part image series so that the latter does not contain any direct heat flow 13 from the excitation source 9, the start image $T_s$ between the characteristic thermal images $T_1$, $T_2$ is selected. The start image $T_S$ is determined as the thermal image which has a heat flow $W_S$, which after the minimum, exceeds the following threshold value $W_{start\_thd}$ (start threshold) in the time course of the recorded heat flow 11 for the first time. For the threshold value $W_{start\_thd}$:

$$W_{start\_thd} = W_{min} + (W_{max} - W_{min}) * \theta$$

applies, wherein $\theta$ is designated as the separation factor. The separation factor $\theta$ is determined empirically and is in the range between 0 and 1, in particular between 0 and 0.15.

To dynamically determine the series length $N_S$, at least two images are used as the references from an image quantity, which contains the characteristic thermal images $T_1$, $T_2$ and the start image $T_S$. The series length $N_S$ may, for example, be selected as twice the length between the start image $T_S$ and the second characteristic thermal image $T_2$. Furthermore, the series length $N_S$ may, for example, be selected as the next greatest length, which is a power of two and thus exceeds the length between the characteristic thermal images $T_1$, $T_2$. In each case, the series length $N_S$ of the part series should be determined such that the end of the series of thermal images is not exceeded.

An amplitude or a phase image may be used, for example, as the result image. An amplitude image is preferably used for defects of the first defect type. The calculation of result images of various types is described, for example, in "Theory and Practice of Infrared Technology for Non-destructive Testing" (Xavier P. V. Maldague, John Wiley & Sons, Inc. 2001), to which reference is made.

The curve discussion of the feature vector W(N) is carried out, for example, with the aid of morphological filters, which ensure perfect separation of various characteristic points, such as, for example minima and maxima. Thus, all minima and maxima of the feature vector W(N) can be determined independently of the total course. The watershed transformation can be used, for example, as the morphological filter and is described in the book "Morphologische Bildverarbeitung" by Pierre Soille, Springer Verlag, Berlin 1998, to which reference is made.

Figure 3:
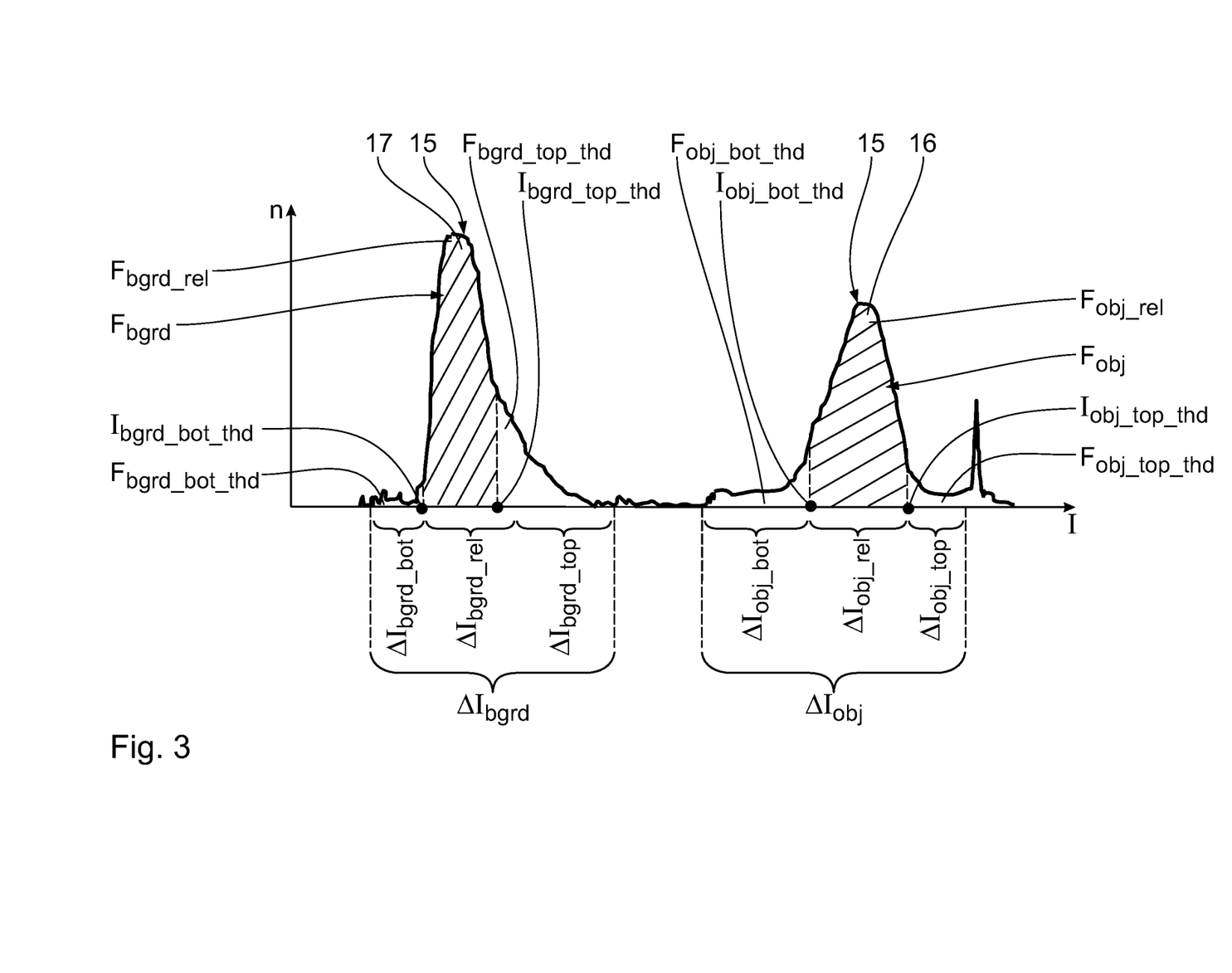
FIG. 3 shows a histogram of a recorded image.

For visual control and for further automatic processing of the thermal images $T_{F1}$ to $T_{F4}$ and the result images, which are used to detect and evaluate the welding seam 4, the latter are automatically converted into an 8 bit image conventional for image processing. The images used have high dynamics. FIG. 3 shows a histogram n(I) of a highly dynamic image, for example one of the thermal images $T_{F1}$ to $T_{F4}$. The frequency of occurrence n is plotted in the histogram n(I) over the intensity I. The histogram curve 15 of the image has a plurality of frequency maxima, which correspond to an image object 16, an image background 17 as well as disturbances present on the image.

To dynamically convert the image, an object intensity region $\Delta I_{obj}$, which corresponds to the image object 16 to be examined, and a background intensity region $\Delta I_{bgrd}$, which corresponds to the image background 16, are firstly determined. This may be carried out, for example, with the aid of morphological filters, which ensure disturbance-free evaluation of the histogram curve 15. It is advantageous to use morphological filters because the histogram curve 15 does not describe a smooth curve but a discrete and thus discontinuous curve. Furthermore, the histogram curve 15 has several minima and maxima which can be reliably determined by means of morphological filters. Watershed transformation can for example be used as morphological filter. Calculated from the object-intensity region $\Delta I_{obj}$ is the total area content $F_{obj}$, which is located between the histogram curve 15 and the intensity axis. Accordingly, the total area content $F_{bgrd}$, located between the histogram curve 15 and the intensity axis, is calculated from the background intensity region $\Delta I_{bgrd}$. A lower local object intensity region $\Delta I_{obj\_bot}$ and an upper local object intensity region $\Delta I_{obj\_top}$, which contains disturbances or random noise values are then detected in the object intensity region $\Delta I_{obj}$. These local objects intensity regions $\Delta I_{obj\_bot}$, $\Delta I_{obj\_top}$ in each case have a characteristic area portion $F_{obj\_bot\_thd}$ or $F_{obj\_top\_thd}$ of the total area content $F_{obj}$. To determine the local object intensity regions $\Delta I_{obj\_bot}$, $\Delta I_{obj\_top}$, a first lower limit value $I_{obj\_bot\_thd}$ and a first upper limit value $I_{obj\_top\_thd}$ are determined in the histogram curve 15 and delimit a portion relevant to information, in other words an intensity region $\Delta I_{obj\_rel}$, relevant to information, of the intensity region $\Delta I_{obj}$. The object intensity region $\Delta I_{obj\_rel}$ forms the basis relevant to information for the image object 16.

A lower local background intensity region $\Delta I_{bgrd\_bot}$ and an upper local intensity region $\Delta I_{bgrd\_top}$ with corresponding second characteristic area portions $F_{bgrd\_bot\_thd}$ or $F_{bgrd\_top\_thd}$ of the total area content $F_{bgrd}$ of the background intensity region $\Delta I_{bgrd}$ are determined in a corresponding manner in the background intensity region $\Delta I_{bgrd}$. For this purpose, a second lower limit value $I_{bgrd\_bot\_thd}$ and a second upper limit value $I_{bgrd\_top\_thd}$, which delimit a portion relevant to information, in other words an intensity region $\Delta I_{bgrd\_rel}$, relevant to information, of the background intensity region $\Delta I_{bgrd}$ are dynamically determined in a corresponding manner from the histogram curve 15. The intensity region $\Delta I_{bgrd\_rel}$ thus forms a basis relevant to information for the image background 17.

The characteristic area portions $F_{bgrd\_bot\_thd}$, $F_{bgrd\_top\_thd}$, $F_{obj\_bot\_thd}$ and $F_{obj\_top\_thd}$ may, for example, in each case be 2.5% of the total area content $F_{bgrd}$ or $F_{obj}$, so the respective remaining area content $F_{bgrd\_rel}$ or $F_{obj\_rel}$ in each case have an area portion of 95%.

The intensity regions $\Delta I_{bgrd\_rel}$ and $\Delta I_{obj\_rel}$ together form the basis relevant to information of the content of the recorded image. Thus, an adaptive dynamic conversion of this image is ensured independently of the image obtaining method and the size of the image object 16 to be examined or its image background 17 and the disturbances which have occurred, in that the content of the recorded image is adequately shown in different dynamics, in particular in the 8 bit dynamics. The absolute limit values $I_{bgrd\_bot\_thd}$, $I_{bgrd\_top\_thd}$, $I_{obj\_bot\_thd}$ and $I_{obj\_top\_thd}$ are used as image-specific threshold values for the dynamic conversion of the image. The conversion of the image to be examined into an 8 bit image can be executed on the obtained basis relevant to information of the content of the recorded image by means of different standard methods of the image processing. Thereby, the conversion can be carried out linearly, logarithmical or according to an application specific method.

The method according to the invention allows automatic, contactless and disturbance-free inspection of the welding seam 4, in which the welding seam 4 to be examined can be explicitly detected and evaluated in relation to various defects 5, 6, 7 and 8 independently of their sizes, positions and defect types and the disturbances which have occurred. Moreover, the method according to the invention can be flexibly and rapidly adjusted under industrial conditions.

The invention claimed is:

1. A method for the automatic inspection of a welding seam using heat flow thermography,
   in which an object, which is to be examined, with a welding seam is provided,
   wherein the object is excited by means of at least one excitation source, and
   the heat flow produced by the excitation is detected in a series of thermal images using at least one infrared sensor, wherein
   feature vector (W(N)) is produced, which is a time course of the detected heat flow
   wherein a first characteristic thermal image ($T_1$) is dynamically determined from the series of thermal images using the feature vector (W(N)), and the first characteristic thermal image ($T_1$) has a minimum heat flow ($W_{min}$) through the object, and
   a second characteristic thermal image (T2) is dynamically determined from the series of thermal images using the feature vector (W(N)), and the second characteristic thermal image ($T_2$) has a maximum heat flow ($W_{max}$) through the object, and
   wherein a heat flow directly from the excitation source to the characteristic thermal images ($T_1$, $T_2$) has already dissipated, if it is apparent from the series of thermal images, and
   a suitable thermal image ($T_{F1}$, $T_{F2}$, $T_{F3}$, $T_{F4}$) from the series of thermal images is used to detect and evaluate the welding seam with respect to defects of various defect types, for each defect type, the characteristic thermal images ($T_1$, $T_2$) being used as references to determine the respective suitable thermal image ($T_{F1}$, $T_{F2}$, $T_{F3}$, $T_{F4}$);
   wherein a thermal image, which was detected before the first characteristic thermal image ($T_1$) and has a maximum heat flow ($W_{max}$) of the excitation source is used for detecting defects of a second defect type as a suitable thermal image ($T_{F2}$), the defects of the second defect type being continuous defects of the welding seam.

2. A method according to claim 1, wherein the second characteristic thermal image ($T_2$) is used for detecting defects of a first defect type as the suitable thermal image ($T_{F1}$), the defects of the first defect type being geometric defects of the welding seam.

3. A method according to claim 1, wherein a start image ($T_s$) being used for detecting defects of a first defect type is dynamically detected in such a way,
   that the start image ($T_s$) is located between the first and the second characteristic thermal image ($T_1$, $T_2$) and has a heat flow ($W_s$), which exceeds a first threshold value ($W_{start\_thd}$) in the time course of the detected heat flow for the first time, wherein for the first threshold value ($W_{start\_thd}$):
   $W_{start\_thd} = W_{min} + (W_{max} - W_{min})*\theta$, applies, wherein
   $W_{start\_thd}$ means first threshold value,
   $W_{min}$ means minimum heat flow, having the first characteristic thermal image ($T_1$),
   $W_{max}$ means maximum heat flow, having the second characteristic thermal image (T2),
   $\theta$ means separation factor,
   wherein a part series of suitable thermal images from the series is selected from the start image ($T_s$) and a series length ($N_s$),
   wherein a result image is obtained from the part series, and
   wherein the defects of the first defect type are geometric defects of the welding seam and the result image is used to detect and evaluate them.

4. A method according to claim 3, wherein the separation factor ($\theta$) is determined in the range between 0 and 1.

5. A method according to claim 3, wherein the separation factor ($\theta$) is determined in the range between 0.1 and 0.15.

6. A method according to claim 3, wherein at least two images from an image quantity, which contains the first characteristic thermal image ($T_1$), the second characteristic thermal image ($T_2$) and the start image ($T_s$), are used as references to dynamically determine the series length ($N_s$).

7. A method according to claim 1, wherein a thermal image, which is located between the first and the second characteristic thermal image ($T_1$, $T_2$) and has a heat flow ($W_{F3}$), which exceeds a second threshold value ($W_{inside\_thd}$) in the time course of the detected heat flow for the first time, is used for detecting defects of a third defect type as the suitable thermal image ($T_{F3}$), wherein for the second threshold value ($W_{inside\_thd}$):
   $W_{inside\_thd} = W^{min} + (W_{max} - W_{min}) \cdot \zeta$, applies, wherein
   $W_{inside\_thd}$ means second threshold value,
   $W_{min}$ means minimum heat flow, having the first characteristic thermal image ($T_1$),
   $W_{max}$ means maximum heat flow, having the second characteristic thermal image ($T_2$),
   $\zeta$ means first heat flow factor,
   the defects of the third defect type being defects located in the interior of the welding seam.

8. A method according to claim 7, wherein the first heat flow factor ($\zeta$) is determined in the range between 0 and 1.

9. A method according to claim 7, wherein the first heat flow factor ($\zeta$) is determined in the range between 0.6 and 0.9.

10. A method according to claim 1, wherein a thermal image, which is located between the first and the second characteristic thermal image ($T_1$, $T_2$) and has a heat flow ($W_{F4}$), which exceeds a third threshold value ($W_{surf\_thd}$) in the time course of the detected heat flow for the first time, is used for detecting defects of a fourth defect type as the suitable thermal image ($T_{F4}$), wherein for the third threshold value (W surf—thd):

$W_{surf\_thd} W_{min} + (W_{max} - W_{min}) \cdot \zeta$, applies, wherein
  $W_{surf\_thd}$ means third threshold value,
  $W_{min}$ means minimum heat flow, having the first characteristic thermal $W_{max}$ image ($T_1$),
  $W_{max}$ means maximum heat flow, having the second characteristic thermal image ($T_2$), and
  $\zeta$ means second heat flow factor, the defects of the fourth defect type being surface defects of the welding seam.

11. A method according to claim 10, wherein the second heat flow factor ($\zeta$) is determined in the range between 0 and 1.

12. A method according to claim 10, wherein the second heat flow factor ($\zeta$) is determined in the range between 0.1 and 0.4.

13. A method according to claim 1, wherein at least one of the images ($T_{F1}$, $T_{F2}$, $T_{F3}$, $T_{F4}$), which are used to detect and evaluate the welding seam in relation to defects of various defect types, is converted into an 8 bit image, wherein
  a histogram (n(I)) of the image ($T_{F1}$, $T_{F2}$, $T_{F3}$, $T_{F4}$) is produced,
  a first portion ($\Delta I_{obj\_rel}$) relevant to information of a first intensity region ($\Delta I_{obj}$), which corresponds to an image object, is determined from the histogram (n(I)),
  wherein a first lower limit value ($I_{obj\_bot\_thd}$) and a first upper limit value ($I_{obj\_top\_thd}$) are dynamically determined, and
  wherein the first limit values ($I_{obj\_bot\_thd}$, $I_{obj\_top\_thd}$) delimit first characteristic area portions ($F_{obj\_bot\_thd}$, $F_{obj\_top\_thd}$) of an area ($F_{obj}$) of the histogram (n(I)) corresponding to the first intensity region ($\Delta I_{obj}$),
  a second portion ($\Delta I_{bgrd\_rel}$) relevant to information of a second intensity region ($\Delta I_{bgrd}$) which corresponds to an image background, is determined from the histogram (n(I)),
  wherein a second lower limit value ($I_{bgrd\_bot\_thd}$) and a second upper limit value ($I_{bgrd\_top\_thd}$) are dynamically determined, and
  wherein the second limit values ($I_{bgrd\_bot\_thd}$, $I_{bgrd\_top\_thd}$) delimit second characteristic area portions ($F_{bgrd\_bot\_thd}$, $F_{bgrd\_top\_thd}$) of an area ($F_{bgrd}$) of the histogram (n(I)) corresponding to the second intensity region ($\Delta I_{bgrd}$), and
  the portions ($\Delta I_{obj\_rel}$, $\Delta I_{bgrd\_rel}$) relevant to information are used as a basis for the conversion of the image (TH, TF2, TF3, TF4) to be examined into an 8 bit image.

14. A method according to claim 13, wherein the first characteristic area portions ($F_{obj\_bot\_thd}$, $F_{obj\_top\_thd}$) in relation to the area ($F_{obj}$) corresponding to the first intensity region ($\Delta I_{obj}$) are determined in the range between 0 and 0.5.

15. A method according to claim 13, wherein the first characteristic area portions ($F_{obj\_bot\_thd}$, $F_{obj\_top\_thd}$) in relation to the area ($F_{obj}$) corresponding to the first intensity region ($\Delta I_{obj}$) are determined in the range between 0.05 and 0.4.

16. A method according to claim 13, wherein the second characteristic area portions ($F_{bgrd\_bot\_thd}$, $F_{bgrd\_top\_thd}$) in relation to the area ($F_{bgrd}$) corresponding to the second intensity region ($\Delta I_{bgrd}$) are determined in the range between 0 and 0.5.

17. A method according to claim 13, wherein the second characteristic area portions ($F_{bgrd\_bot\_thd}$, $F_{bgrd\_top\_thd}$) in relation to the area ($F_{bgrd}$) corresponding to the second intensity region ($\Delta I_{bgrd}$) are determined in the range between 0.05 and 0.4.

18. A method according to claim 13, wherein the characteristic area portions ($F_{obj\_bot\_thd}$, $F_{obj\_top\_thd}$, $F_{bgrd\_bot\_thd}$, $F_{bgrd\_top\_thd}$) are determined independently of one another.

19. A method according to claim 1, wherein at least one of the feature vector (W(N)) and a histogram (n(I)) are processed with the aid of at least one morphological filter.

* * * * *